(12) United States Patent
Ginger

(10) Patent No.: US 7,897,334 B2
(45) Date of Patent: Mar. 1, 2011

(54) SKIN TREATMENT

(75) Inventor: Rebecca Susan Ginger, Wirral (GB)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 2066 days.

(21) Appl. No.: 10/140,694

(22) Filed: May 8, 2002

(65) Prior Publication Data

US 2003/0124553 A1 Jul. 3, 2003

(30) Foreign Application Priority Data

May 9, 2001 (GB) .................................. 0111324.0

(51) Int. Cl.
*C12Q 1/68* (2006.01)
*C12P 19/34* (2006.01)
*C07H 21/04* (2006.01)

(52) U.S. Cl. ............. 435/6; 436/63; 435/91.2; 536/23.1; 536/24.3

(58) Field of Classification Search ............. 435/6, 91.1, 435/91.2; 536/23.1, 24.3
See application file for complete search history.

(56) References Cited

U.S. PATENT DOCUMENTS

| | | | |
|---|---|---|---|
| 4,290,944 | A | 9/1981 | Goldberg |
| 4,302,386 | A | 11/1981 | Stevens |
| 4,998,617 | A | 3/1991 | Ladd, Jr. et al. |
| 5,459,039 | A | 10/1995 | Modrich et al. |
| 5,593,826 | A | 1/1997 | Fung et al. |
| 2001/0051344 | A1 * | 12/2001 | Shalon et al. ..................... 435/6 |

FOREIGN PATENT DOCUMENTS

| | | |
|---|---|---|
| EP | 0 615 745 A1 | 9/1994 |
| WO | 94/10323 | 5/1994 |
| WO | 94/16101 | 7/1994 |

OTHER PUBLICATIONS

Nirunsuksiri et al. " Reduced Stability and Bi-Allelic, Coequal Expression of Profilaggrin mRNA in Keratinocytes Cultured From Subjects with Ichthyosis Vulgaris", J. Investigative Dermatologyt, vol. 110, No. 6, Jun. 1998, pp. 854-861.*
Gan et al. "Organization, Structure, and Polymorphisms of the Human Profilaggrin Gene", Biochemistry, 1990, 29, 9432-9440.*
Markova et al. "Profilaggrin Is a Major Epidermal Calcium-Binding Protein", Mol. Cell. Biol., Jan. 1993, vol. 13, p. 613-625.*
Kroese et al. Genetics in Medicine, vol. 6 (2004), p. 475-480.*
Lucentini the Scientist, 2004, vol. 18, p. 20.*
Nirunsuksiri, W., et al. "Reduced Stability and Bi-Allelic, Coequal Expression of Profilaggrin mRNA is Keratinocytes Cultured From Subjects With Ichthyosis Vulgaris", J. Invest. Dermatol. 110:854-861 © 1998 by the Society for Investigative Dermatology, Inc.
Presland, Richard B., et al., "Characterization of the Human Epidermal Profilaggrin Gene", J. Biol. Chem., vol. 267, No. 33, Issue of Nov. 25, pp. 23772-23781, © 1992 by The American Society for Biochemistry and Molecular Biology, Inc.
Gan, Song-Qing et al., "Organization, Structure, and Polymorphisms of the Human Profilaggrin Gene", 1990, Biochemistry, vol. 29, No. 40, pp. 9432-9440.
Mischke, Dietmar, et al., "Genes Encoding Structural Proteins of Epidermal Corminification and S100 Calcium-Binding Proteins Form a Gene Complex ("Epidermal Differentiation Complex") on Human Chromosome 1q21", J. Invest. Dermatol., 106:989-992, © 1996.
Culver, Kenneth W., et al. "In Vivo Gene Transfer with Retroviral Vector-Producer Cells for Treatment of Experimental Brain Tumors", Science, vol. 256, pp. 1550-1552, Jun. 1992.
Landegren, Ulf, et al. "A Ligase-Mediated Gene Detection Technique", Reports, vol. 241, pp. 1077-1080, Aug. 1988.
Hazra, A.K., "Protein Determinators With Trinitrobenzene Sulfonate: A Method Relatively Independent of Amino Acid Composition", Analytical Biochemistry 137, 437-443 (1984).
Marks, R. "Histochemical Applications of Skin Surface Biopsy", Br. J. Derm. (1972) 86, pp. 20-26.
van Schie, Rob C.A.A., et al., "Saliva: a convenient source of DNA for anlaysis of bi-allelic polymorphisms of Fcy receptors IIA (CD32) and Fcy receptor IIIB (CD16)", J. of Immunological Methods, 208 (1997), 91-101.
Myers, Richard M., et al., "Detection of Single Base Substitutions by Ribonuclease Cleavage at Mismatches in RNA:DNA Duplexes", Science, vol. 230, (1985) 1242-1246.
Kwoh, D.Y., et al., "Transcription-based amplification system and detection of amplified human immunodeficiency virus type 1 with a bead-based sandwich hybridization format", Proc. Natl. Acad. Sci. USA Biochemistry, vol. 86, pp. 1173-1177, Feb. 1989.
Guatelli, John C., "Isothermal, in vitro amplication of nucleic acids by a multienzyme reaction modeled after retroviral replication", Proc. Natl. Acad. Sci. USA Biochemistry, vol. 87, pp. 1874-1878, Mar. 1990.
Saiki, Randall K., et al., "Genetic analysis of amplified DNA with immobilized sequence-specific oligonucleotide probes", Proc. Natl. Acad. Sci. USA Genetics, vol. 86, pp. 6230-6234, Aug. 1989.
Cotton, Richard G. H., et al. "Reactivity of cytosine and thymine in single-base-pair mismatches with hydroxylamine and osmium tetroxide and its application to the study of mutations", Proc. Natl. Acad. Sci. USA Genetics, vol. 85, pp. 4397-4401, Jun. 1988.
Nickerson, Deborah A., et al. "Automated DNA diagnostics using an ELISA-based oligonucleotide ligation assay", Proc. Natl. Acad. Sci. USA Genetics, vol. 87, pp. 8923-8927, Nov. 1990.
Sanger, F., et al. "DNA sequencing with chain-terminating inhibitors", Proc. Natl. Acad. Sci. USA Biochemistry, vol. 74, pp. 5463-5467, Dec. 1977.
Maxam, Allan M., et al. "A new method for sequencing DNA", Proc. Natl. Acad. Sci. USA Biochemistry, vol. 74, No. 2, pp. 560-564, Feb. 1977.

(Continued)

Primary Examiner — Sarae Bausch
(74) Attorney, Agent, or Firm — Michael P. Aronson

(57) ABSTRACT

The present invention provides a method for determining the predisposition of an individual to a skin condition comprising identifying the profilaggrin alleles present in the genome of an ex vivo sample taken from the individual. Skin conditions include the ability of an individual to produce Natural Moisturising Factors (NMF), dry skin and/or predisposition to detergent-induced erythema. Typically profilaggrin alleles are identified by determining the number of encoded filaggrin repeats. Methods of the invention are particularly useful for grouping individuals for the purposes of participation in clinical trials or for matching an individual to a cosmetic preparation.

9 Claims, 8 Drawing Sheets

OTHER PUBLICATIONS

Goodchild, John, et al. "Inhibition of human immunodeficiency virus replication by antisene oligodeoxynucleotides", *Proc. Natl. Acad. Sci. USA* Biochemistry, vol. 85, pp. 5507-5511, Aug. 1988.

Wagner, Ernst, et al. "Transferrin-polycation conjugates as carriers for DNA uptake into cells", *Proc. Natl. Acad. Sci. USA* Biochemistry, vol. 87, pp. 3410-3414, May 1990.

Cotten, Matt, et al. "High-efficiency receptor-mediated devliery of small and large (48 ilobase gene constructs using the endosome-disruption activity of defective or chemically inactivated adenovirus particles", *Proc. Natl. Acad. Sci. USA* Biochemistry, vol. 89, pp. 6094-6098, Jul. 1992.

Bischoff, James R., et al. "An Adenovirus Mutant That Replicates Selectively in p53-Deficient Human Turmor Cells", *Science*, vol. 274, pp. 373-376, Oct. 1996.

Innis et al., *PCR Strategies*, (1995), Academic Press, Inc., N.Y.

Dieffenbach et al., *PCR Primer: A Laboratory Manual*, 133-141 (1995).

Altschul et al., *Methods of Enzymology*, 266, 460-480, (1996).

Ausubel et al., *Short Protocols in Molecular Biology*, 2-36-2-42 (1995).

Cronin et al., *Human Mutation*, 7:244-255 (1996).

Lizardi et al., Exponential Amplification of Recombinant-RNA Hybridization Probes, *Bi-Technology* 6:1197-1202 (1988).

Naeve et al., Accuracy of Automated DNA Sequencing: A Multi-Laboratory Comparison of Sequencing Results, *BioTechniques*, 19:3, 448-453 (1995).

Cohen et al., Emerging Technologies for Sequencing Antisense Oligonucleotides: Capillary Electrophoresis and Mass Spectrometry, *Adv. Chromatog.* 36:127-162.

Griffin et al., DNA Sequencing—Recent Innovations and Future Trends, *Appl. Biochem. Biotechnol.* 38:147-159, (1993).

Saleeba et al., Chemical Cleavage of Mismatch to Detect Mutations, *Methods Enzymol.* 217:286-295 (1992).

Hsu et al., Detection of DNA point mutations with DNA mismatch repair enzymes, *Carcinogenesis* 15:1657-1662 (1994).

Saiki et al., Analysis of enzymatically amplified β-globlin and HLA-DQα DNA with allele-specific oligonucleotide probes, *Nature*, 324:163-167 (1986).

Tobe et al., Single-well genotyping of diallelic sequence variations by a two-color ELISA-based oligonucleotide ligation assay, *Nucleic Acids Res.* 24:3728-3732 (1996).

Witters et al., Antisense oligonucleotides to the epidermal growth factor receptor, *Breast Cancer Res. Treat.* 53:41-50 (1999).

Frankel et al., Antisense oligonucleotide-induced inhibition of adrenocorticotropic hormone release from cultured human corticotrophs, *J. Neusosurg.* 91:261-267 (1999).

Kuriyama et al., A Potential Approach for Gene Therapy Targeting Hepatome Using a Liver-Specific Promoter on a Retroviral Vector, *Cell Struc. and Func.*16:503-510 (1991).

Miller et al., Targeted vectors for gene therapy, *The Faseb J.* 9:190-199 (1995).

Nassander et al., In Vivo Targeting of OV-TL 3 Immunoliposomes to Ascitic Ovarian Carcinoma Cells (OCVAR-3) in Athymic Nude Mice, *Cancer Res.* 52:646-653 (1992).

Martin et al., Irreversible Coupling of Immunoglobin Fragments to Preformed Vesicles, *J. Biol. Chem.* 257:286-288 (1982).

Curiel, D.T., Adenovirus Facilitation of Molecular Conjugate-Mediated Gene Transfer, *Prog. Med. Virol.* 40:1-18 (1993).

Ledley, F.D., Nonviral Gene Therapy: the Promise of Genes as Pharmaceutical Products, *Human Gene Therapy* 6:1129-1144 (1995).

Michael et al., Addition of a short peptide ligand to the adenovirus fiber protein, *Gene Therapy* 2:660-668 (1995).

*International Search Report* No. PCT/EP 02/05070, dated Feb. 6, 2003, 4 pp.

Database EBI accession No. AL356504—EMBL 'Online!' May 21, 2000—Laird, G. "Human DNA sequence from clone RP1-14N1 on chromosome 1q21.1-21.3. Contains ESTs, GSSs and STSs. Contains the FLG gene for profilaggrin and part of a gene for a novel S-100/IcaBP type calcium binding domain protein similar to trichohyalin. n."—XP002228350.

Gan, S-Q. et al. "Organization, Structure, and Polymorphisms of the Human Profilaggrin Gene," *Biochemistry, Am. Chemical Soc.*, vol. 29, No. 40, pp. 9432-9440 (1990).—XP002030710.

Nirunsuksiri, Wilas et al., "Reduced Stability and Bi-allelic, Coequal Expression of Profilaggrin mRNA in Keratinocytes Cultured from Subjects With Ichthyosis Vulgaris," *Journal of Invest. Dermatol.* vol. 110, No. 6, pp. 854-861, (1998).—XP002228348.

Presland, R.B. et al., "Loss of Normal Profilaggrin and Filaggrin in Flaky Tail (ft/ft) Mice: An Animal Model for the Filaggrin-deficient Skin Disease Ichthyopsis Vulgaris," *Journal of Invest. Dermatol.*, vol. 115, No. 6, pp. 1072-1081, (2000).—XP002228349.

* cited by examiner

FIG 1
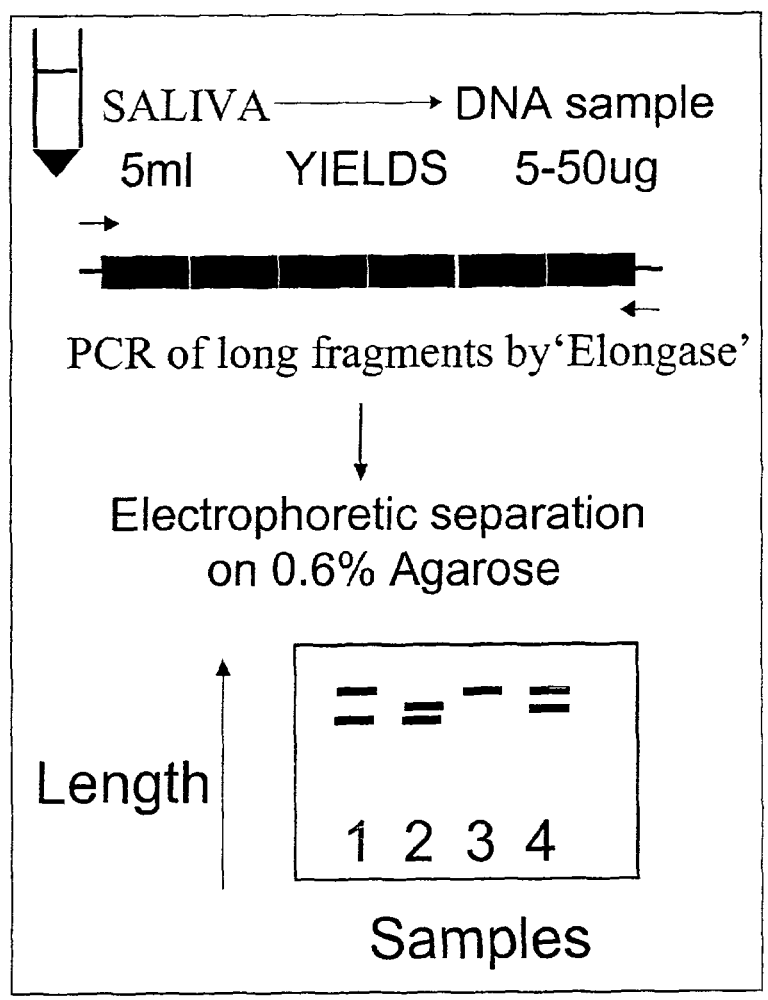
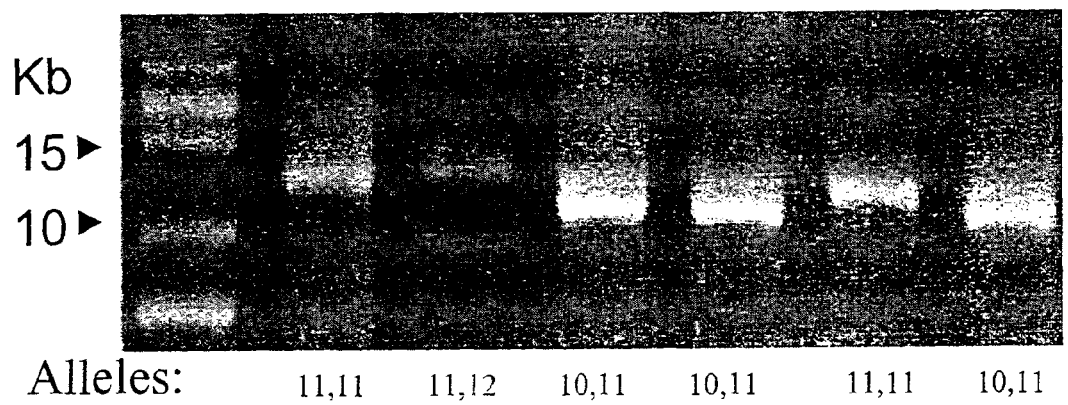

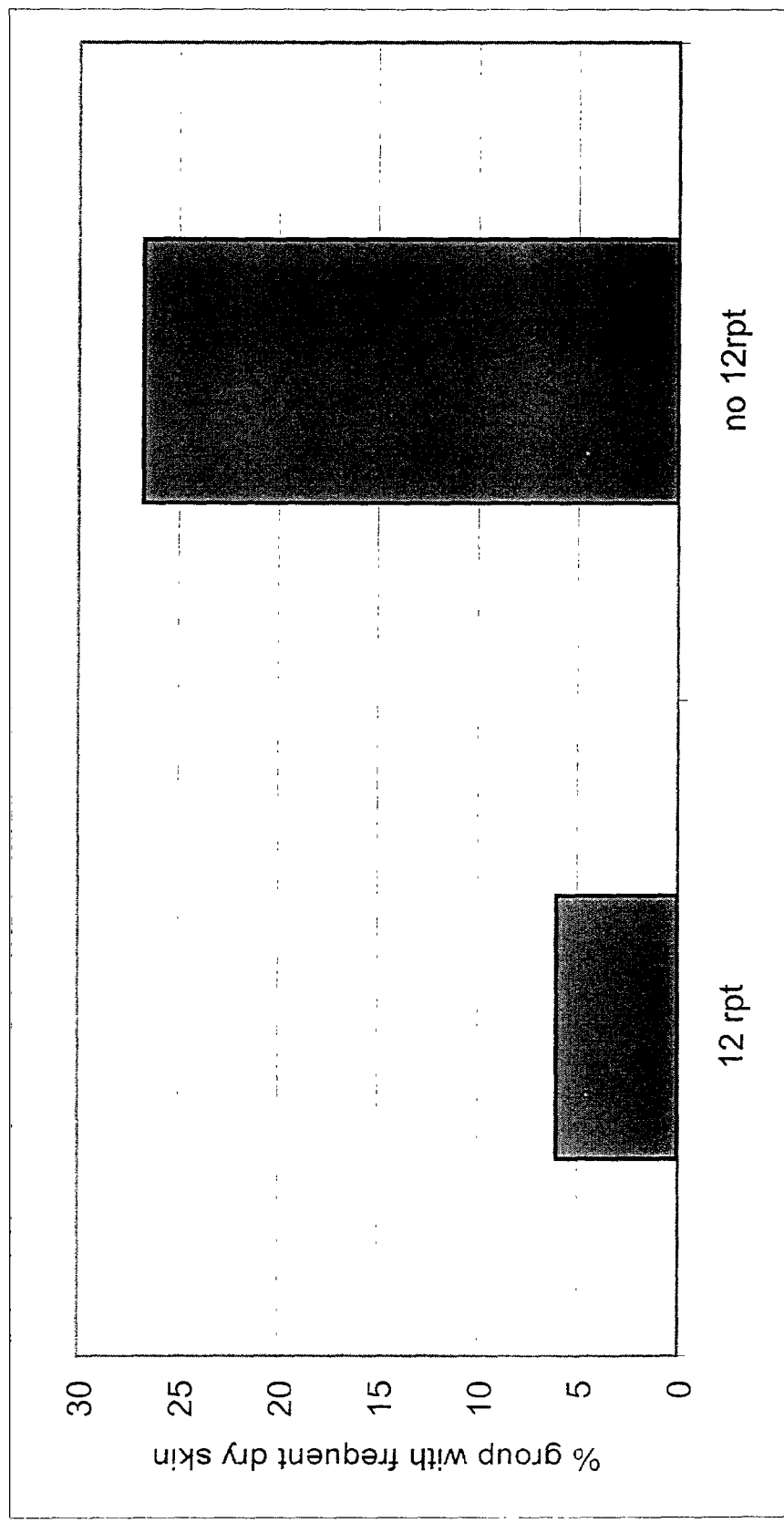

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Flanking probe

<400> SEQUENCE: 1
ggatgaagcc tatgacacca c                                              21

<210> SEQ ID NO 2
<211> LENGTH: 21
<212> TYPE: DNA
<213> ORGANISM: Artificial Sequence
<220> FEATURE:
<223> OTHER INFORMATION: Flanking probe

<400> SEQUENCE: 2
gacaggaaaa gataacttcc c                                              21
```

SKIN TREATMENT

FIELD OF THE INVENTION

The present invention relates to a method of allele identification. More particularly the present invention relates to a method for identifying the profilaggrin alleles present in the genome of an individual, knowledge of which can be used to determine the individual's predisposition to skin conditions.

BACKGROUND OF THE INVENTION

During epidermal differentiation, keratinocytes undergo a well defined series of morphological and biochemical changes in which actively proliferating basal cells differentiate stepwise through the spinous and granular cell layers to eventually form the anuclear squames characteristic of the protective stratum corneum at the skin surface (Presland et al (1992) *J Biol Chem,* 267(33), 23772-23781). Each epidermal layer is characterised by the expression of specific biochemical markers of which the keratin intermediate filament proteins, K5/K14 and K1/K10, predominate in the basal and spinous layers, respectively (Presland et al (1992) *J Biol Chem,* 267(33), 23772-23781).

Granular cells are characterised by the expression of profilaggrin. The profilaggrin gene encodes a high molecular weight phosphorylated polyprotein, composed of a number of related but nonidentical filaggrin repeats. Peptide mapping and sequencing studies have revealed that filaggrin units are separated by short linker peptides which are removed during proteolytic processing (Presland et al (1992) *J Biol Chem,* 267(33), 23772-23781). Like its rodent counterparts, the coding region of the human profilaggrin gene contains no introns within the repetitive portion of the coding region.

Phosphorylated profilaggrin is non-functional and accumulates as F-keratohyalin granules late in epidermal differentiation (Gan et al (1990) *Biochemistry,* 29, 9432-9440). During the transition from the granular to the terminally differentiated cornified cell, profilaggrin is dephosphorylated and proteolytically processed to yield filaggrin monomers. Filaggrin participates in the aggregation of keratin intermediate filaments into the dense macrofibrils characteristic of the stratum corneum (Presland et al (1992) *J Biol Chem,* 267 (33), 23772-23781). Profilaggrin may also play a role in maintaining epidermal hydration through the degradation of filaggrin to free amino acids (Presland et al (1992) *J Biol Chem,* 267(33), 23772-23781). The free amino acids form part of the Natural Moisturising Factors (NMF) of stratum corneum. NMF maintains the hydration of the skin and hence its condition.

The profilaggrin gene is located on Chromosome 1q21 as part of the cluster of genes known as the Epidermal Differentiation Complex (EDC) (Mishke et al (1996) *SID* 106(5): 989-992). Many of these genes encode products which are believed to contribute to stratum corneum structure and function. The profilaggrin gene has been reported to be polymorphic in size due to allelic differences in the number of filaggrin repeats located in exon 3 (Gan et al (1990) *Biochemistry,* 29, 9432-9440). Within the human population 3 length variants of the profilaggrin gene have been identified, encoding multimers of 10, 11 or 12 repeats. It has been shown that both profilaggrin alleles are expressed at approximately equal levels, ie, that expression from the profilaggrin gene is bi-allelic (Nirunsuksiri et al (1998) *Journal of Investigative Dermatology,* 110(6), 854-861)

The allelic differences of profilaggrin genes in individuals affected by ichthyosis vulgaris (IV), a scaling skin disorder inherited as a dominant trait, were compared to unaffected, related or age- and sex-matched normal controls (Nirunsuksiri et al (1998) *Journal of Investigative Dermatology,* 110(6), 854-861). Estimation of the size and number of repeats was performed utilising the EcoRV restrictions sites that flank the entire coding region. The number of filaggrin domains was shown to vary between 10 and 12 in both IV and control individuals and no obvious difference in the distribution of alleles was seen between the two groups (Nirunsuksiri et al (1998) *Journal of Investigative Dermatology,* 110(6), 854-861) suggesting that the profilaggrin genotype of an individual has no influence on the skin condition of that individual. This view is further supported by Gan et al (1990, *Biochemistry,* 29, 9432-9440) who note that it would appear that normal terminally differentiated human epidermis is not critically dependent on the precise amount of functional filaggrin produced from the precursor gene.

Against this background it has been surprisingly shown a correlation between the number of filaggrin repeats and the predisposition to dry skin. We have shown that there is a relationship between profilaggrin genotype and ability of skin to withstand surfactant challenge (ie, predisposition to detergent-induced erythema). It has also been demonstrated that there is a direct correlation between the number of filaggrin repeats and the production of NMF. An individual's ability to produce NMF and/or predisposition to a skin condition such as dry skin, dandruff and/or detergent-induced erythema can be determined by identifying the profilaggrin alleles present in their genome. Individuals can be grouped during clinical trials based their profilaggrin genotype. Individuals can be matched with appropriate cosmetic products based on their profilaggrin genotype.

SUMMARY OF THE INVENTION

Accordingly the present invention provides a method for determining the predisposition of an individual to a skin condition comprising identifying the profilaggrin alleles present in the genome of an ex vivo sample taken from the individual.

The invention also provides a system for determining the predisposition of an individual to a skin condition comprising means for identifying the profilaggrin alleles present in the genome of a sample taken from the individual.

The invention also provides a method for increasing NMF production and/or treating or preventing dry skin and/or dandruff comprising administering a polypeptide comprising the sequence of a profilaggrin, or a variant or fragment thereof or a polynucleotide that encodes any of these. In a preferred embodiment the method is for treating or preventing detergent-induced erythema. Preferably the polypeptide comprises the sequence of a profilaggrin allele having 12 filaggrin repeats.

The invention also provides a polypeptide comprising the sequence of a profilaggrin allele, or a variant or fragment thereof or a polynucleotide that encodes any of these for use in medicine. Preferably the polypeptide comprises the sequence of a profilaggrin allele having 12 filaggrin repeats.

The invention also provides the use of polypeptide comprising the sequence of a profilaggrin allele, or a variant or fragment thereof or a polynucleotide that encodes any of these in the manufacture of a composition (for example a cosmetic composition or a medicament) for treating a skin condition. Preferably the polypeptide comprises the sequence of a profilaggrin allele having 12 filaggrin repeats.

The invention also provides a polynucleotide comprising the SEQ ID NO: 1: 5' GGA TGA AGC CTA TGA CACCAC 3' or SEQ ID NO: 2: 5' GA CAG GAA AAG ATA ACT TCC C 3'. The invention also provides the use of such a polynucleotide in determining the predisposition of an individual to a skin condition.

The invention also provides a method for identifying personal care products that are suitable for an individual to use comprising identifying the profilaggrin genotype of an individual and selecting personal care products known to be suitable for use with the thus determined profilaggrin genotype.

The invention also provides a diagnostic kit comprising means for identifying the profilaggrin alleles present in the genome of a sample taken from the individual.

DETAILED DESCRIPTION OF THE INVENTION

The present invention addresses the need to determine how an individual's skin will respond to conditions such as environmental conditions, or contact with personal care products such as skin care products, cosmetics, cleansing products or hair care products or household products such as fabric detergents, fabric softeners, dishwashing detergents and the like. Example of skin care products include but are not limited to moisturisers, fake tanning preparations, sun tan lotions, massage oils, bath oils, perfumes, balms, creams, face packs, shaving foams and gels. Examples of cosmetics include but are not limited to lipsticks, foundation, eye-shadow, eyeliner, blusher and concealer. Examples of cleansing products include but are not limited to shampoos (in particular anti-dandruff shampoos), soap, personal wash products including shower gel and bubble bath and fabric detergents and dishwashing detergents. Examples of hair care products include but are not limited to hair styling mousses, hair styling sprays, hair styling gels, hair conditioners or hair colourants.

By assessing the profilaggrin genotype of an individual it is possible to determine the individual's predisposition to a skin condition. By "profilaggrin genotype" is meant the identity of profilaggrin alleles in the genome of the individual. Individuals tested by a method of the invention are typically mammalian. In one embodiment the mammal may be a rodent. In another embodiment the mammal may be a human. Thus individuals tested by a method of the invention are diploid and so comprise two copies of the profilaggrin gene within their genome. If an individual has two identical copies of a profilaggrin gene then they are homozygous for that allele. If an individual has two different copies of a profilaggrin gene, i.e. one is polymorphic to the other, then the individual is heterozygous for that allele. By "predisposition" is meant that the presence of an individual profilaggrin allele in the genome of an individual, or the combination of profilaggrin alleles present in the genome of an individual, are associated with, or are predictive of, a skin condition.

The term "skin condition" as used herein includes within its meaning all physical parameters of the skin, including the scalp, such as moisture retention, substance production or barrier formation. In one embodiment the term "skin condition" refers to the ability of the skin to maintain healthy levels of NMF production. Accordingly, the invention provides a method of determining the presdisposition of an individual to maintain a healthy level of NMF production. To put it another way the invention provides a method of determining the individual's susceptibility to conditions related to aberrant NMF production. Typically skin conditions caused or exacerbated by aberrant NMF production are caused by the production of less NMF than by healthy skin. Conditions associated with aberrant filaggrin and NMF production include Ichthyosis Vulgaris. In another embodiment the term "skin condition" refers to dry skin. Dry skin conditions include senile/postmenopausal xerosis, surfactant induced xerosis, winter xerosis, sunburn. In another embodiment the term "skin condition" refers to conditions of the scalp such as dandruff. In another embodiment the term "skin condition" refers to erythema, such as detergent-induced erythema.

Thus the method of the invention provides a means for categorising individuals by the characteristics of their skin. This can be useful in both therapeutic and non-therapeutic applications. In one embodiment methods of the invention are used for therapeutic applications. In another embodiment methods of the invention are used for non-therapeutic applications, such as cosmetic applications.

Therapeutic applications of methods of the invention include means of diagnosing the cause of a medical skin condition. Accordingly the method of treatment for the medical skin condition can be tailored to complement the individual's phenotype. Therapeutic applications of methods of the invention also include means of determining whether an individual's skin is likely to react adversely to a pharmaceutical preparation, such as a topically administered pharmaceutical preparation. In that case the individual can be matched to a particular pharmaceutical preparation in order to provide maximum therapeutic benefit whilst minimising or avoiding any undesirable effects on the condition of the individual's skin.

Non-therapeutic applications of methods of the invention include means of grouping individuals for the purposes of trials for agents, for example, cosmetics or any other form of preparation introduced to the body. This can be useful for interpreting the results obtained from such trials, for example where the reaction of the skin of different individuals during the trial is not uniform. The heterogeneity of responses might be interpreted more clearly by grouping or stratifying individuals according to their predisposition to skin conditions. The skilled person will appreciate that using this method it may be possible to develop agents that are suitable for use with some individuals but not suitable with others. Accordingly a panel of agents can be built up, which panel includes different agents having suitability for use with different individuals. Following the trials, individuals wishing to use such an agent can use a method of the invention to determine which agents are most suitable for use based on their own predisposition to skin conditions. Thus the method of the invention allows an individual to be matched with a personal care product such as those listed above.

Methods of identifying the profilaggrin genotype of an individual are performed on biological material of the individual. Preferably the biological material is removed from the individual prior to performing the method of identification. In other words, typically the biological material is ex vivo. The ex vivo material may be further cultured in vitro prior to performing the method.

An ex vivo sample may comprise tissue or cells taken from any part of the body. A preferred ex vivo sample comprises material taken from the circulatory system, or material taken from a bodily cavity, such as the oral cavity. A particularly preferred ex vivo sample is a saliva sample. The alleles present in an individual can be determined from a saliva sample using methods known in the art, such as that described in Schie and Wilson (1997, *Journal of Immunological Methods*, 208, 91-101).

Accordingly the ex vivo sample may be provided by an individual without need for specialised collection means. For example, a saliva sample or buccal swab can be simply provided by the individual prior to testing.

The profilaggrin gene and protein are well known in the art and are described above and in Gan et al (1990, *Biochemistry,* 29, 9432-9440). Numerous profilaggrin sequences have been deposited in publicly accessible databases.

A profilaggrin gene comprises multilple filaggrin repeats, usually 10, 11 or 12 repeats. The filaggrin repeats are typically of the same length (972 bp, 324 amino acids in humans) as each other, although this is less typical of filaggrin repeats at the 5'- and 3'-ends of the mRNA. The filaggrin repeats may display considerable sequence variation, typically of from 0-50%, more typically of from 2-30%, yet more typically of from 10-15%, between repeats on the same allele and between different alleles. Usually variations are attributable to a single-base change but may also involve a change in charge (Gan et al (1990) *Biochemistry,* 29, 9432-9440). A consensus amino acid sequence map of a human filaggrin repeat is known (Gan et al (1990) *Biochemistry,* 29, 9432-9440) and preferably a filaggrin repeat will have at least 50%, more preferably at least 75%, more preferably 90%, yet more preferably at least 95% sequence identity to that consensus sequence or a variant of the consensus sequence shown in Gan et al (1990, *Biochemistry,* 29, 9432-9440). Normally the amino acid sequences encoding the amino and carboxy termini are more conserved, as are the 5' and 3' DNA sequences flanking the coding portions of the gene (Presland et al (1992) *J Biol Chem,* 267(33), 23772-23781).

The presence of different profilaggrin alleles in the genome of an individual can be identified by methods well known in the art for distinguishing between macromolecules with divergent structures. The term "allele" as used herein with respect to profilaggrin refers to any profilaggrin gene comprising a polymorphism. In a preferred embodiment the term "allele" with respect to profilaggrin refers to a profilaggrin gene identifiable by the number of filaggrin repeats it encodes. However, the skilled person will appreciate that many other polymorphisms of the profilaggrin gene are possible and all profilaggrin alleles are included within the scope of the invention. For example, the different phenotypes observed between individuals having profilaggrin alleles encoding profilaggrin with 10, 11 or 12 filaggrin repeats may be a direct result of the differences in production of filaggrin. However, the skilled person will appreciate that the number of filagrgin repeats may instead be a 'marker' for some other sequence polymorphism in the different profilaggrin alleles, or in another gene within the epidermal differentiation complex. Thus the phenotype may not be directly related to the number of filaggrin repeats present. Thus it will be appreciated that methods described herein will be suitable to identify differences between any profilaggrin alleles and that the invention is not restricted to polymorphism in respect of the number of filaggrin repeats.

Accession number M60494 identifies the 3' end of a human profilaggrin gene (and is the amino terminus sequence of profilaggrin disclosed in Gan et al (1990, *Biochemistry,* 29, 9432-9440) and includes both EF-hands, intron 2, the N-terminus and truncated repeat and the first full filaggrin repeat ending at linker 2.

Accession number LO1089 identifies exons 2-3 of the human profilaggrin gene (and is the amino terminus sequence of profilaggrin disclosed in Presland et al (1992) *J Biol Chem,* 267(33), 23772-23781). It contains EF-hand 2 (EF-hand 1 is in exon 1 L01088), the truncated repeat, the first linker and about half of the first full filaggrin repeat.

Accession number AH003056 identifies the carboxy terminus sequence of profilaggrin (it combines M60501.1, M60502.1 and M60503.1 as published by Gan et al (1990, *Biochemistry,* 29, 9432-9440) and includes the last full filaggrin repeat, truncated repeat, c-terminus and poly A tail.

Typically an allele may be identified at the polynucleotide level, such as by analysis of genomic DNA or mRNA. The skilled person is well aware of methods for determining the presence or absence of different polynucleotides. Methods known for determining the presence or absence of particular RNA sequences include northern blots, reverse transcription and PCR (RT-PCR) and ribonuclease protection assays (Sambrook and Russell, (2001) Molecular Cloning: A Laboratory Manual. 3rd edition, Cold Spring Harbour Laboratory Press, New York, USA). Methods known for determining the presence or absence of particular DNA sequences include sequencing, Southern blots, PCR amplification of genomic DNA and analysis of restriction fragment length polymorphisms (RFLPs). See Sambrook and Russell (2001, Molecular Cloning: A Laboratory Manual. 3rd edition, Cold Spring Harbour Laboratory Press, New York, USA), Innis et al, (1995, *PCR Strategies,* Academic Press, Inc.: NY); Dieffenbach et al (1995, *PCR Primer: A Laboratory Manual,* New York: Cold Spring Harbor Press). DNA sequence analysis may also be achieved by detecting alteration in electrophoretic mobility of DNA fragments in gels with or without denaturing agents. Differences can also be visualized by high resolution gel electrophoresis or distinguished according to differences in DNA sequence melting points. See, e.g., Myers et al (1982, *Science,* 230, 1242). Methods for detecting the presence of specific sequences include detection techniques such as fluorescence-based detection methods, immune-based assays such as RIA, antibody staining such as Western blot analysis or in situ hybridization, using appropriately labeled probe.

Sequences useful for constructing probes suitable for use in detecting the presence of a sequence of interest include any nucleic acid sequence having at least about 50%, preferably at least 70%, more preferably at least 80% or greater sequence identity or homology with the sequence of a known profilaggrin gene or fragment thereof by a Blast search. "Percent (%) sequence identity" or "percent (%) sequence homology" is defined as the percentage of nucleic acid residues in a candidate sequence that are identical with the nucleic acid residues of the sequence of interest, after aligning the sequences and introducing gaps, if necessary to achieve maximum percent sequence identity, and not considering any conservative substitutions as part of the sequence identity. Methods for performing sequence alignment and determining sequence identity are known in the art, may be performed without undue experimentation, and calculations of % identity values may be obtained for example, using available computer programs such as WU-BLAST-2 (Altschul et al, 1996, *Methods in Enzymology* 266,460-480). One may optionally perform the alignment using set default parameters in the computer software program (Blast search, MacVector and Vector NTI). Based upon the restriction map of a particular allele, a banding pattern can be predicted when the Southern blot is hybridized with a probe which recognizes the sequence of interest. The level of stringency of hybridization used can vary depending upon the level of sensitivity desired, a particular probe characteristic, such as probe length and/or annealing temperature, or degree of homology between probe sequence and sequence of interest. Therefore, considerations of sensitivity and specificity will determine stringency of hybridization required for a particular assay.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperatures. The higher the degree of desired homology between the probe and hybridizable sequence, the higher the relative temperature that can be used. For additional details and explanation of stringency of hybridization reactions, see Ausubel et al (1995, *Current Protocols in Molecular Biology,* Wiley Interscience Publishers) or Protocols Online (URL: www.protocol-online.net/molbio/index.htm).

"Stringent conditions" or "high-stringency", as defined herein, may be identified by those that: (1) use low ionic strength and high temperature for washing, for example 0.1× SSC, 0.2% SDS at 65-70° C.

"Moderately-stringent conditions" may be identified as described by Sambrook and Russell (2001, Molecular Cloning: A Laboratory Manual, 3rd edition), and include the use of washing solution and hybridisation conditions (e.g. temperature, ionic strength, and % SDS) less stringent that those described above. An example of moderately stringent conditions is 0.2×SSC, 0.1% SDS at 58-65° C. The skilled artisan will recognise how to adjust temperature, ionic strength, etc. as necessary to accommodate factors such as probe length, degree of homology between probe and target site and the like. Therefore, in addition to the sequence of interest, it is contemplated that additional or alternative probe sequences which vary from that of the sequence of interest will also be useful in screening for the sequence of interest.

In a preferred embodiment profilaggrin alleles are identified by the number of filaggrin repeats present. Thus typically the method of identifying the profilaggrin alleles present in the genome of an individual comprises determining whether the alleles present have 10, 11 or 12 filaggrin repeats.

In one preferred embodiment allele identification is performed using PCR. Forward and reverse primers are prepared using techniques well known in the art and comprise a sequence based on an upstream region and a downstream region, respectively, relative to the sequence of the profilaggrin gene coding sequence encoding polymorphic filaggrin repeats. Preferably the upstream and downstream regions chosen for design of primers will be substantially conserved between different alleles. "Substantially conserved" includes within its meaning sequences having at least 50%, 60%, 70%, 80%, 90%, 95%, ? 98%, 99% or 100% sequence identity. Thus primers can be designed for binding to similar but non-identical sequences, for example by using degenerate primers or by including nucleotides that have a reduced specificity for the purposes of complementarity, such as inosine, within the primer. Preferably one, or more preferably both, of the forward and reverse primers are 100% identical to the upstream and/or downstream regions of each profilaggrin allele.

Upstream and downstream primers can be derived from the sequences present in publicly available databases. For example, one of the primers used in the examples below is designed in accordance with bases 3112-3132 of the sequence identified by accession number LO1089 (equivalent to bases 1530-1551 of the sequence identified by accession number M60494), whereas the other primer is designed in accordance with bases 3341-3361 of the sequence identified by accession number AH003056.

Amplification of profilaggrin alleles using these primers will produce different sized products dependent of the number of encoded filaggrin repeats. It is thought that a 10 repeat allele should yield a fragment of 11,610 bp, an 11 repeat allele should yield a fragment of 12,582 by and a 12 repeat allele shouls yield a fragment of 13,554 bp. Thus a preferred upstream region used for design of the forward primer is at least a part of the region of the profilaggrin gene encoding the amino terminus or the 5' DNA sequence upstream of the coding portions of the gene. Preferably the sequence of the forward primer is SEQ ID NO: 1: 5' GGA TGA AGC CTA TGA CACCAC 3'.

A preferred downstream region used for design of the reverse primer is at least a part of the region of the profilaggrin gene encoding the caroxy terminus or the 3' DNA sequence downstream of the coding portions of the gene. Preferably the sequence of the reverse primer is SEQ ID NO: 2: 5' GA CAG GAA AAG ATA ACT TCC C 3'.

The PCR reaction is performed in order to amplify DNA obtained from the biological material from the sample taken from the individual. In one embodiment the DNA is genomic DNA extracted from the biological material. In another embodiment the DNA is cDNA which has been reverse transcribed from RNA, typically mRNA, which RNA has been extracted from the biological material. Methods for extracting genomic DNA, methods for extracting RNA, methods for extracting mRNA and methods for reverse transcription of RNA are well known in the art, for example see Sambrook and Russell (2001, Molecular Cloning: A Laboratory Manual. 3rd edition, Cold Spring Harbour Laboratory Press, New York, USA).

In a preferred embodiment the DNA is genomic DNA and the sample is a saliva sample or buccal swab. Methods for extracting DNA from saliva samples and buccal swabs are known in the art (Schie and Wilson (1997) *Journal of Immunological Methods,* 208, 91-101).

The PCR reaction can be performed under conditions well known in the art or as suggested by the manufacturer of a commercially available PCR kit. For example, amplification may be performed using from 0.1 to 30 µg/ml DNA substrate. Amplification may be performed using from 2 µM to 2 mM dNTPs. Amplification may be performed using from 2 µM to 2 mM forward and reverse primers. Amplification may be performed using and from 17 µM to 170 mM $Mg^{2+}$. In a preferred embodiment amplification is performed using about 200 µM dNTPs. In a preferred embodiment amplification is performed using about 200 µM forward and reverse primers. In a preferred embodiment amplification is performed using about 1.7 mM $Mg^{2+}$. By "about" is meant that the concentration used varies by no more than 50%, 25%, 10% or 5% from the concentration stated. Most preferably the PCR reaction is performed essentially as described in the exemplified methods below.

PCR products can then be analysed by any suitable method. Typically the PCR products are analysed by size fractionation, usually using gel electrophoresis performed in accordance with techniques well known in the art (see Sambrook and Russell (2001) Molecular Cloning: A Laboratory Manual. 3rd edition, Cold Spring Harbour Laboratory Press, New York, USA). Most preferably the PCR products are analysed essentially as described in the exemplified methods below.

Other methods suitable for identifying the profilaggrin alleles present in the genome of an individual include allele specific hybridisation; allele specific oligonucleotide hybridisation; and primer specific extension.

Allele specific hybridization uses probes overlapping a region of at least one profilaggrin allele and having about 5, 10, 20, 25 or 30 nucleotides around a polymorphic region. In a preferred embodiment, several probes capable of hybridizing specifically to other profilaggin alleles are attached to a solid phase support, e.g. a "chip," (which can hold up to about 250,000 oligonucleotides). Oligonucleotides can be bound to a solid support by a variety of processes, including lithography. Mutation detection analysis using these chips comprising oligonucleotides, also terms "DNA probe arrays" is described e.g., in Cronin et al (1996, *Human Mutation* 7, 244). In one embodiment, a chip comprises all the allelic variants of at least one polymorphic region of a profilaggrin gene. The solid phase support is then contacted with a test nucleic acid and hybridization to the specific probes is detected. Accordingly, the identity of numerous allelic variants of one or more genes can be identified in a simple hybridization experiment.

These techniques may also comprise the step of amplifying the nucleic acid before analysis. Amplification techniques are known to those of skill in the art and include, but are not limited to cloning, polymerase chain reaction (PCR), polymerase chain reaction of specific alleles (ASA), ligase chain region (LCR), nested polymerase chain reaction, self sustained sequence replication (Guatelli et al (1990) *Proc Natl Acad Sci USA* 87, 1874-1878), transcriptional amplification system (Kwoh et al (1989) *Proc Natl Acad Sci USA* 86, 1173-1177), and Q-Beta Replicase (Lizardi (1988) *Bio/Technology* 6, 1197).

Amplification products may be assayed in a variety of ways, including size analysis, restriction digestion followed by size analysis, detecting specific tagged oligonucleotide primers in the reaction products, allele-specific oligonucleotide (ASO) hybridization, allele specific 5' exonuclease detection, sequencing, hybridization % and the like.

In a merely illustrative embodiment a method of identifying profilaggrin alleles includes the steps of (i) isolating nucleic acid (e.g., genomic, RNA or both) from the cells of a sample collected from an individual (ii) contacting the nucleic acid sample with one or more primers which specifically hybridize 5' and 3' to at least one polymorphism in the profilaggrin allele under conditions such that hybridization and amplification of the polymorphic region of the allele occurs, and (iii) detecting the amplification product. These detection schemes are especially useful for the detection of nucleic acid molecules if such molecules are present in very low numbers.

An allele of profilaggrin may be identified by alterations in restriction enzyme cleavage patterns. For example, sample and control DNA is isolated, amplified (optionally) digested with one or more restriction endonucleases, and fragment length sizes are determined, for example by gel electrophoresis.

In yet another embodiment, any of a variety of sequencing reactions known in the art can be used to directly sequence the allele. Exemplary sequencing reactions include those based on techniques developed by Maxim and Gilbert (1997, *Proc Natl Acad Sci USA* 74, 560) or Sanger et al (1977, *Proc Nat Acad Sci USA* 74, 5463). It is also contemplated that any of a variety of automated sequencing procedures may be utilized when performing the subject assays (see, for example *Biotechniques* (1995) 19, 448), including sequencing by mass spectrometry (e.g. WO 94/16101; Cohen et al (1996) *Adv Chromatogr* 36, 127-162; and Griffin et al (1993) *Appl Biochem Biotechnol* 38, 147-159). It will be evident to one of skill in the art that, for certain embodiments, the occurrence of only one, two or three of the nucleic acid bases need be determined in the sequencing reaction. For instance, A-track or the like, e.g., where only one nucleic acid is detected, can be carried out.

A profilaggrin allele may be identified by using cleavage agents (such as nuclease, hydroxylamine or osmium tetroxide and with piperidine) to detect mismatched bases in RNA/RNA or RNA/DNA or DNA/DNA heteroduplexes (Myers et al (1985) *Science* 230, 1242). In general, the art technique of "mismatch cleavage" starts by providing heteroduplexes formed by hybridizing (labeled) RNA or DNA containing the wild-type allele with a sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size, for example using denaturing polyacrylamide gel to determine the site of mutation. See, for example, Cotton et al (1988) *Proc Natl Acad Sci USA* 85, 4397; and Saleeba et al (1992) *Methods Enzymol* 217, 286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes). For example, the mutY enzyme of *E. coli* cleaves A at G/A mismatches and the thymidine DNA glycosylase from HeLa cells cleaves T at G/T mismatches (Hsu et al. (1994) *Carcinogenesis* 15, 1657-1662). According to an exemplary embodiment, a probe based on a chosen profilaggrin allele is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

Examples of other techniques for detecting alleles include, but are not limited to, selective oligonucleotide hybridization, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al (1986) *Nature* 324, 163; Saiki et al (1989) *Proc Natl Acad Sci USA* 86, 6230). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hyrbidized with labeled target DNA.

In another embodiment, identification of a profilaggrin allele may be carried out using an oligonucleotide ligation assay (OLA), as described, e.g., in U.S. Pat. No. 4,998,617 and in Landegren et al (1988, *Science* 241, 1077-1080). The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson et al have described a nucleic acid detection assay that combines attributes of PCR and OLA (Nickerson et al (1990) *Proc Natl*

*Acad Sci USA* 87, 8923-27). In this method, PCR is used to achieve the exponential amplification of target DNA, which is then detected using OLA.

Several techniques based on this OLA method have been developed and can be used to detect profilaggrin alleles. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al (1997, *Nucleic Acids Res* 24, 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colours.

Once the profilaggrin genotype of an individual has been determined, that individual can be categorised as having a high or low predisposition to a skin condition. Thus methods of the invention can be used to identify the profilaggrin genotype of an individual in order to determine that individual's predisposition to a skin condition. Accordingly the invention provides a system for determining the predisposition of an individual to a skin condition comprising means for identifying the profilaggrin alleles present in the genome of a sample taken from the individual.

In one embodiment the invention provides a polynucleotide comprising the sequence of a primer for use in amplifying the region of the profilaggrin gene comprising a polymorphism. In a preferred embodiment the primer is of SEQ ID NO: 1: 5' GGA TGA AGC CTA TGA CACCAC 3' or SEQ ID NO: 2: 5'GA CAG GAA AAG ATA ACT TCC C 3'.

The invention also provides for the use of a primer of the invention in a method of determining the predisposition of an individual to a skin condition as described above. Thus kits and assay components comprising PCR primers and oligonucleotides for hybridisation as described above form further aspects of the invention.

The primer kit of the present invention is useful for identifying profilaggrin alleles using the polymerase chain reaction. The kit comprises a set of pairs of single stranded DNA primers which can be annealed to sequences flanking the polymorphism and within or surrounding the profilaggrin gene on the relevant chromosome in order to prime amplifying DNA synthesis of the gene itself. The complete set may allow synthesis of all of the nucleotides of the profilaggrin allele coding sequences, ie the exons, or may allow synthesis of less than the entire coding region. The set of primers preferably allows synthesis of both intron and exon sequences, as allelic variations may be found in a profilaggrin gene intron. The kit can also contain DNA polymerase, preferably a thermophilic DNA polymerase, more preferably Taq polymerase, yet more preferably Elongase (GIBCOBRL Life Technologies) and suitable reaction buffers. Such components are known in the art.

In order to facilitate subsequent cloning of amplified sequences, primers may have restriction enzyme sites appended to their 5' ends. Thus, all nucleotides of the primers are derived from profilaggrin gene sequences or sequences adjacent to that gene except the few nucleotides necessary to form a restriction enzyme site. Such enzymes and sites are well known in the art. The primers themselves can be synthesized using techniques which are well known in the art. Generally, the primers can be made using synthesizing machines which are commercially available. Given the sequences of the profilaggrin allelic variations which are known in the art, design of particular primers is well within the skill of the art.

Kits of the invention optionally further comprise a personal care product, such as cosmetic preparation as described above, which preparation is suitable for use on an individual having a particular profilaggrin genotype.

An example of a kit according to the invention may include a means of nucleic acid isolation, such as QIAamp DNA Blood Midi Kit or Epicentre BuccalAmp kit and associated equipment such as a centrifuge, means for DNA quantitation such as a spectrophotometer, means for performing a PCR reaction such as a thermal cycler and means for analysing PCR products such as a gel electrophoresis kit. However, many or all of these items will be readily available in a molecular biology laboratory. Therefore, a kit according to the invention may comprise dNTPs suitable for dilution to a 200 µM final concentration, a pair of oligonucleotide primers such as of SEQ ID NO:1: 5' GGA TGA AGC CTA TGA CACCAC 3' and SEQ ID NO: 2: 5' GA CAG GAA AAG ATA ACT TCC C 3' magnesium chloride solution suitable for filution to 1.7 mM final concentration Mg $^{2+}$ and a thermostable DNA polymerase such as Elongase (GIBCOBRL Life Technologies). The kit may further comprise instructions for using the components and may therefore include instructions for performance of the PCR cycle as follows:

Heat reactions to 94° C. for 5 mins
Add Elongase reaction mix to 1/50 dilution (HOT START)
Start programme

| 5 minutes | 94° C. | 1 cycle |
|---|---|---|
| 30 seconds | 94° C. | |
| 30 seconds | 57° C. | 35 cycles |
| 12 minutes | 68° C. | |
| soak | 4° C. | |

A kit of the invention may further comprise polynucleotides having known sizes for comparison with and sizing of the the PCR products. Such polynucleotides may be, for example, extension ladder markers (such as produced by GIBCO-BRL) or a reference genomic DNA containg previously identified variants.

The present invention also contemplates a method for cosmetic treatment comprising determining the profilaggrin genotype of an individual by a method as described above in order to identify a cosmetic preparation suitable for use with an individual having that profilaggrin genotype and using the thus identified cosmetic preparation on that individual. The use of the cosmetic preparation involves use in the normal manner. Typically this will involve topical application to the skin or scalp of the individual. The cosmetic preparation may be any preparation as described above.

The present invention also contemplates a method for treating a skin condition by influencing the type and/or availability of profilaggrin alleles in the epidermis of an individual. This may be achieved by administering a polypeptide comprising the sequence of a profilaggrin alleles or a variant or fragment thereof. This may also be achieved by administering polynucleotide comprising a sequence that encodes a profilaggrin allele or a variant or fragment thereof. Thus the present invention contemplates a method of modifying, preferably increasing, NMF production in the epidermis of an individual. The present invention also contemplates a method of treating dry skin and/or detergent-induced erythema. The present invention also contemplates a method of treating dandruff. The polypeptide or polynucleotide may be formulated with a cosmetic preparation to enhance the beneficial effects of that cosmetic or to ameliorate the undesirable effects of that cosmetic. Thus in a preferred embodiment, a method of the invention can increase profilaggrin production.

Preferably the profilaggrin allele that is produced has 12 filaggrin repeats.

"Fragments" and "variants" include within their meaning polypeptides that are useful to prepare antibodies which will specifically bind a profilaggrin or mutant forms thereof. It is well known that sequence divergence occurs in the filaggrin repeats (Gan et al (1990) *Biochemistry*, 29, 9432-9440).

A profilaggrin "variant" includes within its meaning a polypeptide wherein at one or more positions there have been amino acid insertions, deletions, or substitutions, either conservative or non-conservative, provided that such changes result in a protein whose basic properties, for example binding activity (type of and affinity), thermostability, activity in a certain pH-range (pH-stability) have not significantly been changed. "Significantly" in this context means that one skilled in the art would say that the properties of the variant may still be different but would not be unobvious over the ones of the original protein. By "conservative substitutions" is intended combinations such as Gly, Ala; Val, Ile, Leu; Asp, Glu; Asn, Gln; Ser, Thr; Lys, Arg; and Phe, Tyr.

A "fragment" is less than 100% of the whole polypeptide. For example, at least 99%, 98%, 95%, 90%, 80%, 60%, 40%, 30%, 25% or 20% of the whole profilaggrin protein.

It will be recognised by those skilled in the art that the polypeptide of the invention may be modified by known polypeptide modification techniques. These include the techniques disclosed in U.S. Pat. No. 4,302,386 issued 24, Nov. 1981 to Stevens, incorporated herein by reference. Such modifications may alter, preferably enhance the immunogenicity of the antigen, or they may have no effect on such immunogenicity. For example, a few amino acid residues may be changed.

Alternatively, smaller polypeptides corresponding to antigenic parts of the polypeptide may be chemically synthesised by methods well-known in the art. These include the methods disclosed in U.S. Pat. No. 4,290,944 issued 22, Sep. 1981 to Goldberg, incorporated herein by reference.

Thus, the polypeptide for use in methods of the invention includes a class of modified polypeptides, including synthetically derived polypeptides or fragments of the original polypeptide, having common elements of origin, structure, and immunogenicity that are within the scope of the present invention.

An isolated polynucleotide for use in a method of the invention may comprise a sequence that encodes a profilaggrin gene or a variant or fragment thereof as described above for use in a method of the invention. As used herein, the term "isolated" means that the gene is in isolation from at least most of the human chromosome on which it is found, in other words the gene is not claimed in the form in which it has previously existed. Thus, the gene of the invention includes the gene when that gene has been cloned into a bacterial vector, such as a plasmid, or into a viral vector, such as a bacteriophage, provided that such clones are in isolation from clones constituting a DNA library of the relevant chromosome.

The "gene" may comprise the promoter and/or other expression-regulating sequences which normally govern its expression and it may comprise introns, or it may consist of the coding sequence only, for example a cDNA sequence.

Alternatively antisense polynucleotides may be used in a method of the invention. Antisense polynucleotides are single-stranded nucleic acids, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene. Recently, formation of a triple helix has proven possible where the polynucleotide is bound to a DNA duplex. It was found that polynucleotides could recognise sequences in the major groove of the DNA double helix. A triple helix was formed thereby. This suggests that it is possible to synthesise sequence-specific molecules which specifically bind double-stranded DNA via recognition of major groove hydrogen binding sites.

By binding to a profilaggrin target nucleic acid, the above polynucleotides can inhibit the function of the target nucleic acid. This could, for example, be a result of blocking the transcription, processing, poly(A) addition, replication, translation, or promoting inhibitory mechanisms of the cells, such as promoting RNA degradations.

Antisense polynucleotides may be prepared in the laboratory and then introduced into cells, for example by microinjection or uptake from the cell culture medium into the cells, or they are expressed in cells after transfection with plasmids or retroviruses or other vectors carrying an antisense gene. Antisense polynucleotides were first discovered to inhibit viral replication or expression in cell culture for Rous sarcoma virus, vesicular stomatitis virus, herpes simplex virus type 1, simian virus and influenza virus. Since then, inhibition of mRNA translation by antisense polynucleotides has been studied extensively in cell-free systems including rabbit reticulocyte lysates and wheat germ extracts. Inhibition of viral function by antisense polynucleotides has been demonstrated in vitro using polynucleotides which were complementary to the AIDS HIV retrovirus RNA (Goodchild, J. 1988 "Inhibition of Human Immunodeficiency Virus Replication by Antisense Oligodeoxynucleotides", *Proc. Natl. Acad. Sci.* (*USA*) 85(15), 5507-11). The Goodchild study showed that polynucleotides that were most effective were complementary to the poly(A) signal; also effective were those targeted at the 5' end of the RNA, particularly the cap and 5' untranslated region, next to the primer binding site and at the primer binding site. The cap, 5' untranslated region, and poly(A) signal lie within the sequence repeated at the ends of retrovirus RNA (R region) and the polynucleotide complementary to these may bind twice to the RNA.

Typically, antisense polynucleotides are 15 to 35 bases in length. For example, 20-mer polynucleotides have been shown to inhibit the expression of the epidermal growth factor receptor mRNA (Witters et al, *Breast Cancer Res Treat* 53:41-50 (1999)) and 25-mer polynucleotides have been shown to decrease the expression of adrenocorticotropic hormone by greater than 90% (Frankel et al, *J Neurosurg* 91:261-7 (1999)). However, it is appreciated that it may be desirable to use polynucleotides with lengths outside this range, for example 10, 11, 12, 13, or 14 bases, or 36, 37, 38, 39 or 40 bases.

The aforementioned polypeptides and polynucleotides or a formulation thereof may be administered by any conventional method including topically to the site of the skin condition, orally or by parenteral (eg subcutaneous or intramuscular) injection. The treatment may consist of a single dose or a plurality of doses over a period of time.

Polynucleotides may be administered systemically. Alternatively the inherent binding specificity of polynucleotides characteristic of base pairing is enhanced by limiting the availability of the polynucleotide to its intended locus in vivo, permitting lower dosages to be used and minimising systemic effects. Thus, polynucleotides may be applied locally to achieve the desired effect. The concentration of the polynucleotides at the desired locus is much higher than if the polynucleotides were administered systemically, and the therapeutic effect can be achieved using a significantly lower total amount. The local high concentration of polynucleotides enhances penetration of the targeted cells and effectively blocks translation of the target nucleic acid sequences.

The polynucleotides can be delivered to the locus by any means appropriate for localised administration of a drug. For example, a solution of the polynucleotides can be injected directly to the site or can be delivered by infusion using an infusion pump. The polynucleotides also can be incorporated into an implantable device which when placed adjacent to the desired site, to permit the polynucleotides to be released into the surrounding locus.

The polynucleotides may be administered via a hydrogel material. The hydrogel is non-inflammatory and biodegradable. Many such materials now are known, including those made from natural and synthetic polymers. In a preferred embodiment, the method exploits a hydrogel which is liquid below body temperature but gels to form a shape-retaining semisolid hydrogel at or near body temperature. Preferred hydrogel are polymers of ethylene oxide-propylene oxide repeating units. The properties of the polymer are dependent on the molecular weight of the polymer and the relative percentage of polyethylene oxide and polypropylene oxide in the polymer. Preferred hydrogels contain from about 10% to about 80% by weight ethylene oxide and from about 20% to about 90% by weight propylene oxide. A particularly preferred hydrogel contains about 70% polyethylene oxide and 30% polypropylene oxide. Hydrogels which can be used are available, for example, from BASF Corp., Parsippany, N.J., under the tradename Pluronic$^R$.

In this embodiment, the hydrogel is cooled to a liquid state and the oligonucleotides are admixed into the liquid to a concentration of about 1 mg polynucleotides per gram of hydrogel. The resulting mixture then is applied onto the surface to be treated, for example by spraying or painting during surgery or using a catheter or endoscopic procedures. As the polymer warms, it solidifies to form a gel, and the polynucleotides diffuse out of the gel into the surrounding cells over a period of time defined by the exact composition of the gel.

The polynucleotides can be administered by means of other implants that are commercially available or described in the scientific literature, including liposomes, microcapsules and implantable devices. For example, implants made of biodegradable materials such as polyanhydrides, polyorthoesters, polylactic acid and polyglycolic acid and copolymers thereof, collagen, and protein polymers, or non-biodegradable materials such as ethylenevinyl acetate (EVAc), polyvinyl acetate, ethylene vinyl alcohol, and derivatives thereof can be used to locally deliver the polynucleotides. The polynucleotides can be incorporated into the material as it is polymerised or solidified, using melt or solvent evaporation techniques, or mechanically mixed with the material. In one embodiment, the polynucleotides are mixed into or applied onto coatings for implantable devices such as dextran coated silica beads, stents, or catheters.

The dose of polynucleotides is dependent on the size of the polynucleotides and the purpose for which is it administered. In general, the range is calculated based on the surface area of tissue to be treated. The effective dose of polynucleotide is somewhat dependent on the length and chemical composition of the polynucleotides but is generally in the range of about 30 to 3000 µg per square centimeter of tissue surface area.

The polynucleotides may be administered systemically for cosmetic, therapeutic and prophylactic purposes. The polynucleotides may be administered by any effective method, for example, parenterally (eg intravenously, subcutaneously, intramuscularly) or by oral, nasal or other means which permit the oligonucleotides to access and circulate in the patient's bloodstream. Polynucleotides administered systemically preferably are given in addition to locally administered polynucleotides, but also have utility in the absence of local administration. A dosage in the range of from about 0.1 to about 10 grams per administration to an adult human generally will be effective for this purpose.

It will be appreciated that antisense agents also include larger molecules which bind to said profilaggrin mRNA or genes and substantially prevent expression of said profilaggrin mRNA or genes and substantially prevent expression of said profilaggrin protein. Thus, expression of an antisense molecule which is substantially complementary to said profilaggrin mRNA is envisaged as part of the invention.

The said larger molecules may be expressed from any suitable genetic construct as is described below and delivered to the patient. Typically, the genetic construct which expresses the antisense molecule comprises at least a portion of the said profilaggrin cDNA or gene operatively linked to a promoter which can express the antisense molecule in the cell.

Although genetic constructs for delivery of polynucleotides can be DNA or RNA it is preferred if it is DNA.

Preferably, the genetic construct is adapted for delivery to a human cell.

Means and methods of introducing a genetic construct into a cell in an animal body are known in the art. For example, the constructs of the invention may be introduced into cells by any convenient method, for example methods involving retroviruses, so that the construct is inserted into the genome of the cell. For example, in Kuriyama et al (1991) *Cell Struc. and Func.* 16, 503-510 purified retroviruses are administered. Retroviral DNA constructs comprising a polynucleotide as described above may be made using methods well known in the art. To produce active retrovirus from such a construct it is usual to use an ecotropic psi2 packaging cell line grown in Dulbecco's modified Eagle's medium (DMEM) containing 10% foetal calf serum (FCS). Transfection of the cell line is conveniently by calcium phosphate co-precipitation, and stable transformants are selected by addition of G418 to a final concentration of 1 mg/ml (assuming the retroviral construct contains a neo$^R$ gene). Independent colonies are isolated and expanded and the culture supernatant removed, filtered through a 0.45 µm pore-size filter and stored at −70° C. For the introduction of the retrovirus into the tumour cells, it is convenient to inject directly retroviral supernatant to which 10 µg/ml Polybrene has been added. For tumours exceeding 10 mm in diameter it is appropriate to inject between 0.1 ml and 1 ml of retroviral supernatant; preferably 0.5 ml.

Alternatively, as described in Culver et al (1992) *Science* 256, 1550-1552, cells which produce retroviruses are injected. The retrovirus-producing cells so introduced are engineered to actively produce retroviral vector particles so that continuous productions of the vector occurred within the tumour mass in situ. Thus, proliferating epidermal cells can be successfully transduced in vivo if mixed with retroviral vector-producing-cells.

Targeted retroviruses are also available for use in the invention; for example, sequences conferring specific binding affinities may be engineered into pre-existing viral env genes (see Miller & Vile (1995) *Faseb J.* 9, 190-199 for a review of this and other targeted vectors for gene therapy).

Other methods involve simple delivery of the construct into the cell for expression therein either for a limited time or, following integration into the genome, for a longer time. An example of the latter approach includes liposomes (Nässander et al (1992) *Cancer Res.* 52, 646-653).

For the preparation of immuno-liposomes MPB-PE (N-[4-(p-maleimidophenyl)butyryl]-phosphatidylethanolamine) is synthesised according to the method of Martin & Papahadjopoulos (1982) *J. Biol. Chem.* 257, 286-288. MPB-PE is incorporated into the liposomal bilayers to allow a covalent coupling of the antibody, or fragment thereof, to the liposomal surface. The liposome is conveniently loaded with the DNA or other genetic construct of the invention for delivery to the target cells, for example, by forming the said liposomes in a solution of the DNA or other genetic construct, followed by sequential extrusion through polycarbonate membrane filters with 0.6 µm and 0.2 µm pore size under nitrogen pressures up to 0.8 MPa. After extrusion, entrapped DNA construct is separated from free DNA construct by ultracentrifugation at 80 000×g for 45 min. Freshly prepared MPB-PE-liposomes in deoxygenated buffer are mixed with freshly prepared antibody (or fragment thereof) and the coupling reactions are carried out in a nitrogen atmosphere at 4° C. under constant end over end rotation overnight. The immunoliposomes are separated from unconjugated antibodies by ultracentrifugation at 80 000×g for 45 min. Immunoliposomes may be injected intraperitoneally or directly into the tumour.

Other methods of delivery include adenoviruses carrying external DNA via an antibody-polylysine bridge (see Curiel Prog. Med. Virol. 40, 1-18) and transferrin-polycation conjugates as carriers (Wagner et al (1990) Proc. Natl. Acad. Sci. USA 87, 3410-3414). In the first of these methods a polycation-antibody complex is formed with the DNA construct or other genetic construct of the invention, wherein the antibody is specific for either wild-type adenovirus or a variant adenovirus in which a new epitope has been introduced which binds the antibody. The polycation moiety binds the DNA via electrostatic interactions with the phosphate backbone. The adenovirus, because it contains unaltered fibre and penton proteins, is internalised into the cell and carries into the cell with it the DNA construct of the invention. It is preferred if the polycation is polylysine.

The DNA may also be delivered by adenovirus wherein it is present within the adenovirus particle, for example, as described below.

In an alternative method, a high-efficiency nucleic acid delivery system that uses receptor-mediated endocytosis to carry DNA macromolecules into cells is employed. This is accomplished by conjugating the iron-transport protein transferrin to polycations that bind nucleic acids. Human transferrin, or the chicken homologue conalbumin, or combinations thereof is covalently linked to the small DNA-binding protein protamine or to polylysines of various sizes through a disulfide linkage. These modified transferrin molecules maintain their ability to bind their cognate receptor and to mediate efficient iron transport into the cell. The transferrin-polycation molecules form electrophoretically stable complexes with DNA constructs or other genetic constructs of the invention independent of nucleic acid size (from short oligonucleotides to DNA of 21 kilobase pairs). When complexes of transferrin-polycation and the DNA constructs or other genetic constructs of the invention are supplied to the tumour cells, a high level of expression from the construct in the cells is expected.

High-efficiency receptor-mediated delivery of the DNA constructs or other genetic constructs of the invention using the endosome-disruption activity of defective or chemically inactivated adenovirus particles produced by the methods of Cotten et al (1992) Proc. Natl. Acad. Sci. USA 89, 6094-6098 may also be used. This approach appears to rely on the fact that adenoviruses are adapted to allow release of their DNA from an endosome without passage through the lysosome, and in the presence of, for example transferrin linked to the DNA construct or other genetic construct of the invention, the construct is taken up by the cell by the same route as the adenovirus particle.

This approach has the advantages that there is no need to use complex retroviral constructs; there is no permanent modification of the genome as occurs with retroviral infection; and the targeted expression system is coupled with a targeted delivery system, thus reducing toxicity to other cell types.

It will be appreciated that "naked DNA" and DNA complexed with cationic and neutral lipids may also be useful in introducing the DNA of the invention into cells of the individual to be treated. Non-viral approaches to gene therapy are described in Ledley (1995) *Human Gene Therapy* 6, 1129-1144.

Alternative targeted delivery systems are also known such as the modified adenovirus system described in WO 94/10323 wherein, typically, the DNA is carried within the adenovirus, or adenovirus-like, particle. Michael et al (1995) *Gene Therapy* 2, 660-668 describes modification of adenovirus to add a cell-selective moiety into a fibre protein. Mutant adenoviruses which replicate selectively in p53-deficient human tumour cells, such as those described in Bischoff et al (1996) *Science* 274, 373-376 are also useful for delivering the genetic construct of the invention to a cell. Thus, it will be appreciated that a further aspect of the invention provides a virus or virus-like particle comprising a genetic construct of the invention. Other suitable viruses or virus-like particles include HSV, AAV, vaccinia and parvovirus.

The genetic constructs of the invention can be prepared using methods well known in the art.

Whilst it is possible for a polypeptides-or polynucleotides to be administered alone, it is preferable to present it as a pharmaceutical formulation, together with one or more acceptable carriers. The carrier(s) must be "acceptable" in the sense of being compatible with the compound of the invention and not deleterious to the recipients thereof.

Typically, the carriers will be water or saline which will be sterile and pyrogen free.

The invention will now be described in more detail by reference to the following Figures and Examples wherein:

FIG. 1 shows the identification of profilaggrin alleles in the genome of an individual using a PCR approach to determine the number of filaggrin repeats.

Figure 4A:
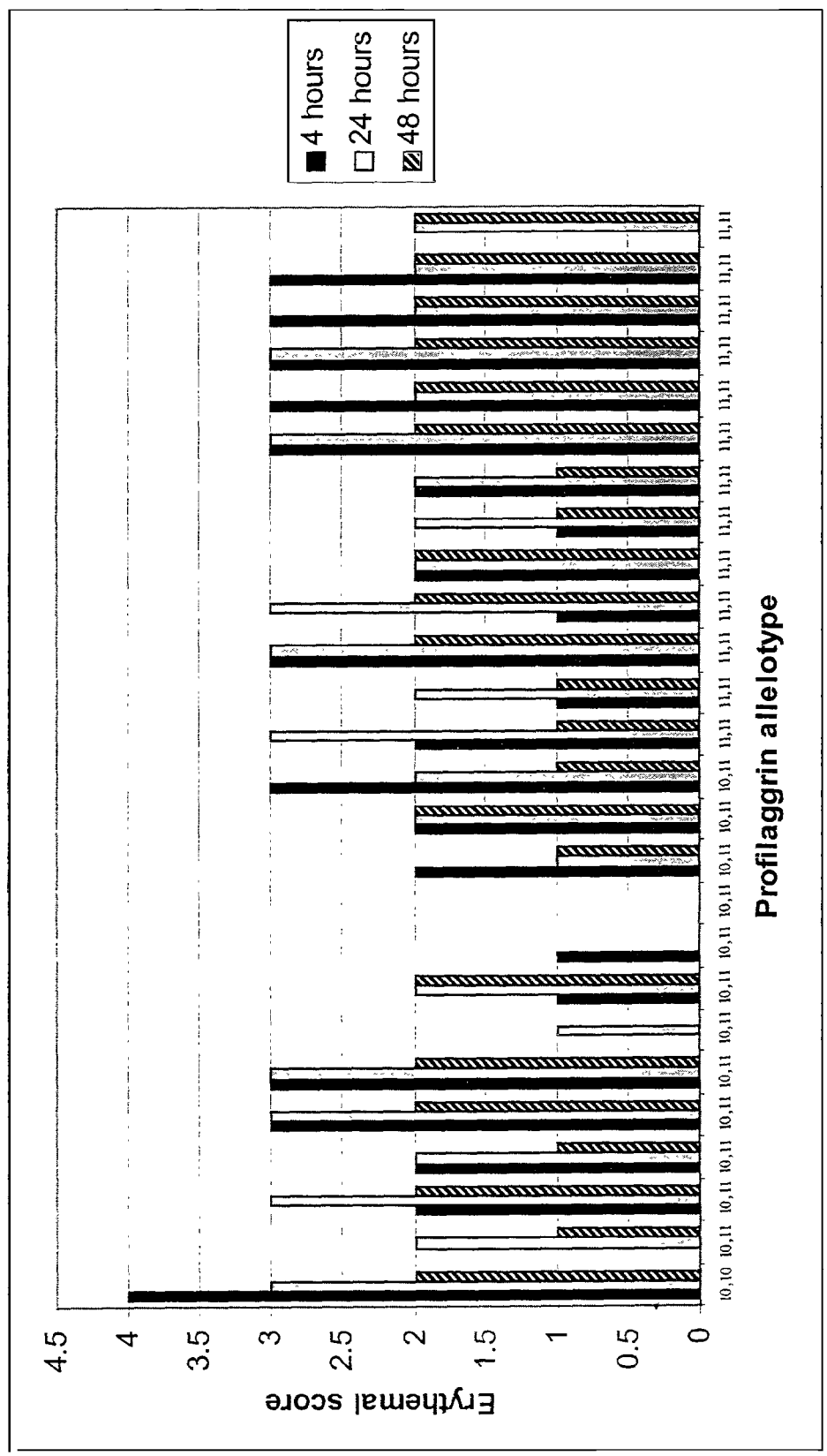
Figure 4B:
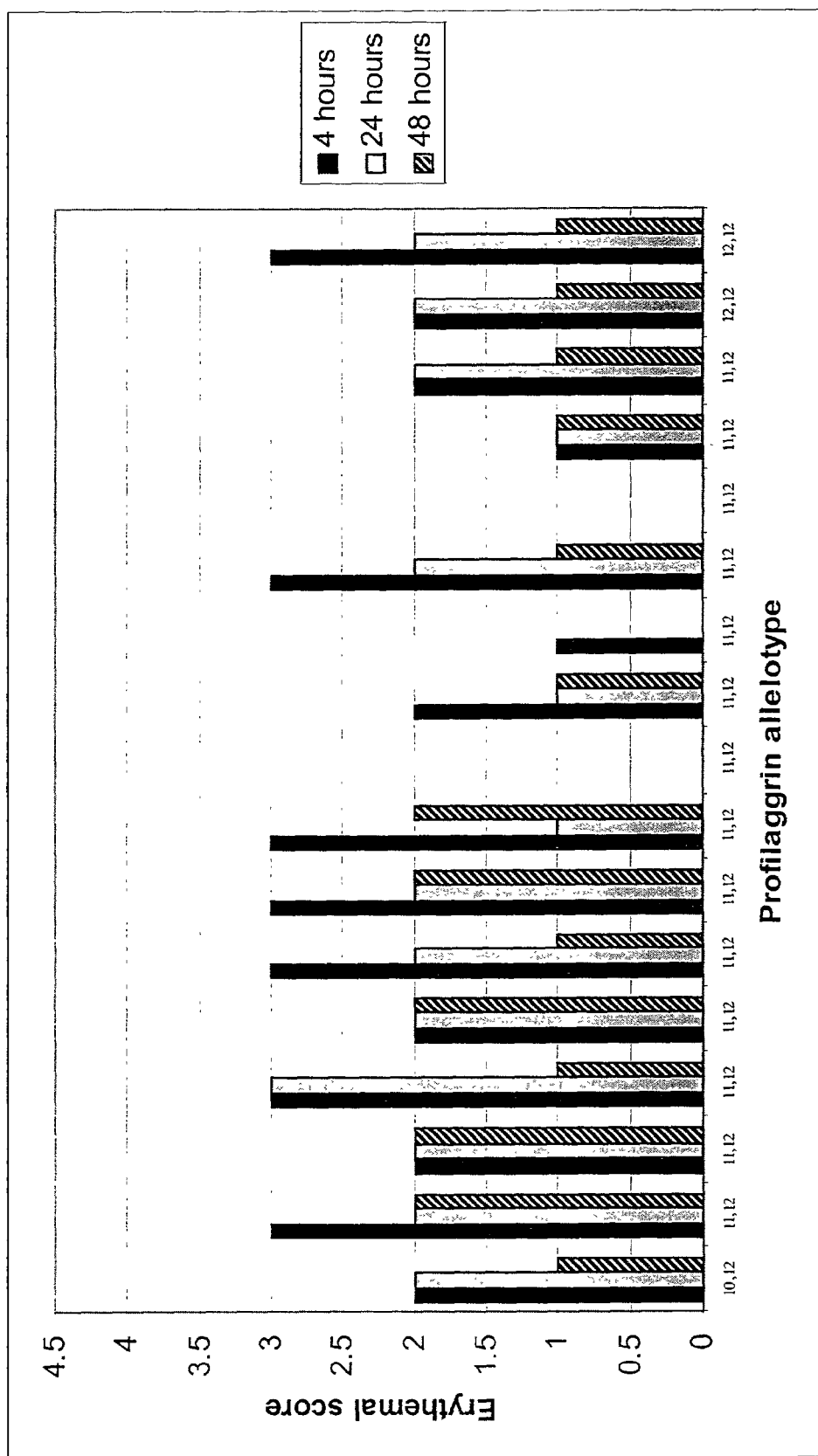

FIG. 4 shows erythemal score 48 hours post patching with 1% SLS versus profilaggrin allelotype. Mann-Whitney Rank Sum Test: There is a statistically significant difference between erythemal scores 24 hours post patch when comparing no 12 repeat allele panellists with 1 or more 12 repeat allele panellists (n=43) (a) SLS patch recovery—individuals with no 12 repeat alleles; (b) SLS patch recovery—individuals with 1 or more 12 repeat alleles.

FIG. 5 shows the proportion of panellists with or without the 12 repeat allele who frequently suffer from self-perceived dry skin. Fisher's Exact test: There is a statistically significant relationship (p=0.0237) between the presence or absence of the 12 repeat allele and frequency of dry skin (n=89).

Figure 6:
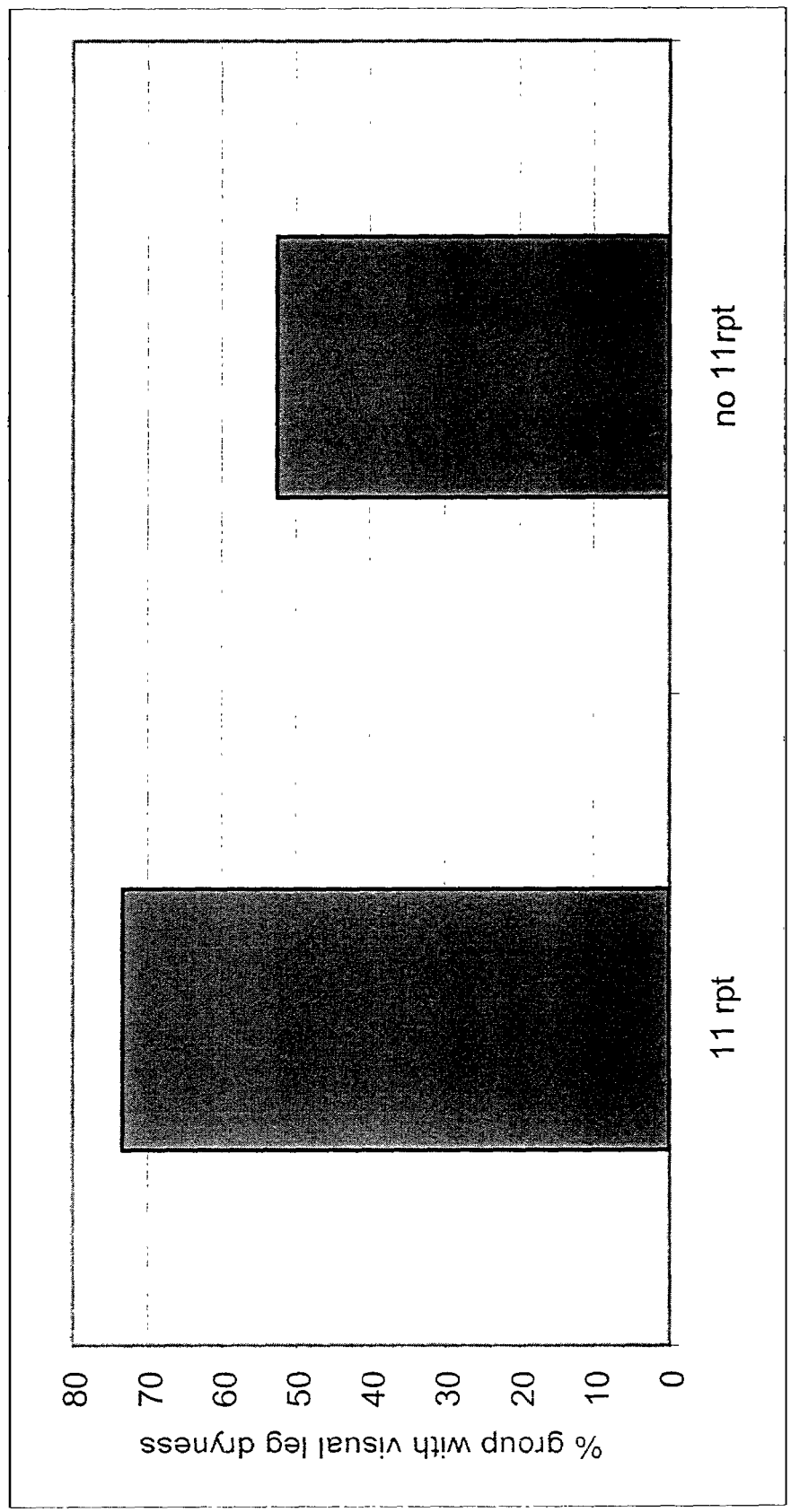

FIG. 6 shows the proportion of panellists with or without the 11 repeat allele who displayed visual leg skin dryness. Fisher's Exact test: There is a statistically significant (p=0.099) relationship between the presence of the 11 repeat allele and the proportion of panellists with visual skin dryness (n=113).

Figure 7:
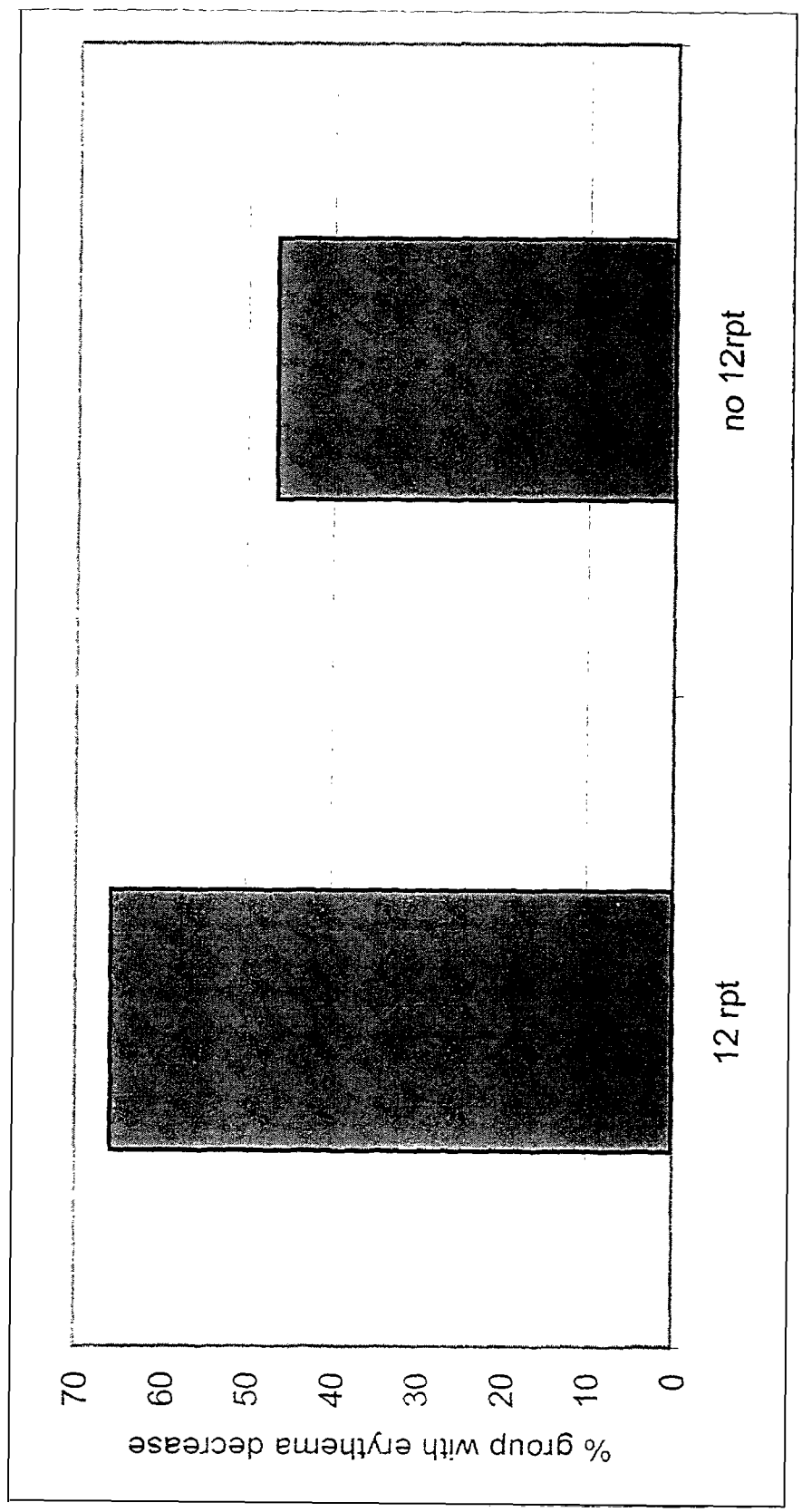

FIG. 7 shows the proportion of panellists with or without the 12 repeat allele who displayed decreased erythema between 4 and 48 hours post patch with 1% SLS. Fisher's Exact test: There is a statistically significant relationship (p=0.0587) between the presence of the 12 repeat allele and decreased erythema post patch (n=131).

EXAMPLES

Methods

DNA isolation was performed using the QIAamp DNA Blood Midi Kit (Qiagen) and the method was adapted for saliva samples as described by Schie and Wilson (1997, *Journal of immunological Methods*, 208, 91-101). 5 ml of saliva was diluted with 5 ml PBS (Sigma) and centrifuged for 5 mins at 3000 g. The supernatant was discarded and the pellet resuspended in 10 ml PBS. The resuspended pellet was centrifuged for 5 mins at 3000 g, the supernatant was discarded and the pellet resuspended in 750 µl PBS. 1 ml kit Lysis buffer and 100 ul kit protease was added according to the kit protocol. 5 µl RNase (7 units/µl) was added followed by mixing and incubation at 70° C. for 20 mins. 1 ml absolute ethanol was added and the kit protocol was followed to purify the DNA. The final preparation was eluted in 300 ul kit elution buffer, and the eluate was re-applied to the column once in order to concentrate the preparation. The eluate was stored in aliquots at −20° C.

DNA quantitation was performed on a 1/10 dilution by spectrophotometric measurements (Sambrook and Russell, (2001) Molecular Cloning: A Laboratory Manual. 3rd edition, Cold Spring Harbour Laboratory Press, New York, USA).

PCR reactions were performed in a 50 µl volume using the following conditions: 150 ng Genomic DNA sample; 200 µM final concentration dNTPs; 200 µM final concentration forward (SEQ ID NO: 1: 5' GGA TGA AGC CTA TGA CAC-CAC 3') and reverse (SEQ ID NO: 2: 5' GA CAG GAA AAG ATA ACT TCC C 3') primers; 1.7 mM final concentration $Mg^{2+}$. For 50 µl Elongase (GIBCOBRL Life Technologies) reaction use 3 ul buffer A+7 ul buffer B. The PCR reaction was performed using the following conditions:

Heat reactions to 94° C. for 5 mins
Add Elongase reaction mix to 1/50 dilution (HOT START)
Start programme:

| 5 minutes | 94° C. | 1 cycle |
|---|---|---|
| 30 seconds | 94° C. | |
| 30 seconds | 57° C. | 35 cycles |
| 12 minutes | 68° C. | |
| soak | 4° C. | |

PCR products were analysed by gel electrophoresis using techniques well known in the art (Sambrook and Russell, (2001) Molecular Cloning: A Laboratory Manual. 3rd edition, Cold Spring Harbour Laboratory Press, New York, USA). Sample loading buffer GIBCO-BRL was added to an aliquot of the PCR product to a 1x final concentration. 20 µl of PCR reaction product was size fractionated on a 0.6% agarose (1×TBE Sigma) gel by electrophoresis at 30V (using extension ladder markers—Life Technologies).

Example 1

A group of 43 randomly selected females provided saliva samples for DNA analysis, and information on skin condition history. Panellists were subjected to a patch of 1% SLS (sodium dodecyl sulfate) for 24 hours and the degree of erythema was scored 4, 24 and 48 hours after the patching. In a separate study a randomly selected mixed gender group of 20 individuals provided saliva samples for DNA analysis, cyanoacrylate biposies (Marks (1972) *British journal of Dermatology* 86:20-26) for NMF analysis and a skin/scalp condition history. Genomic DNA was extracted from the saliva samples and analysed by PCR to determine the profilaggrin genotype for each individual (FIG. 1). The NMF content of the stratum corneum was determined using the standard TNBS assay (Hazra et al 1984 Analytical Biochemistry 137: 437-443) and normalised to total protein.

All three variants were identified with the following frequencies:
10 repeats (18%), 11 repeats (60%, and 12 repeats (22%).

Figure 2:
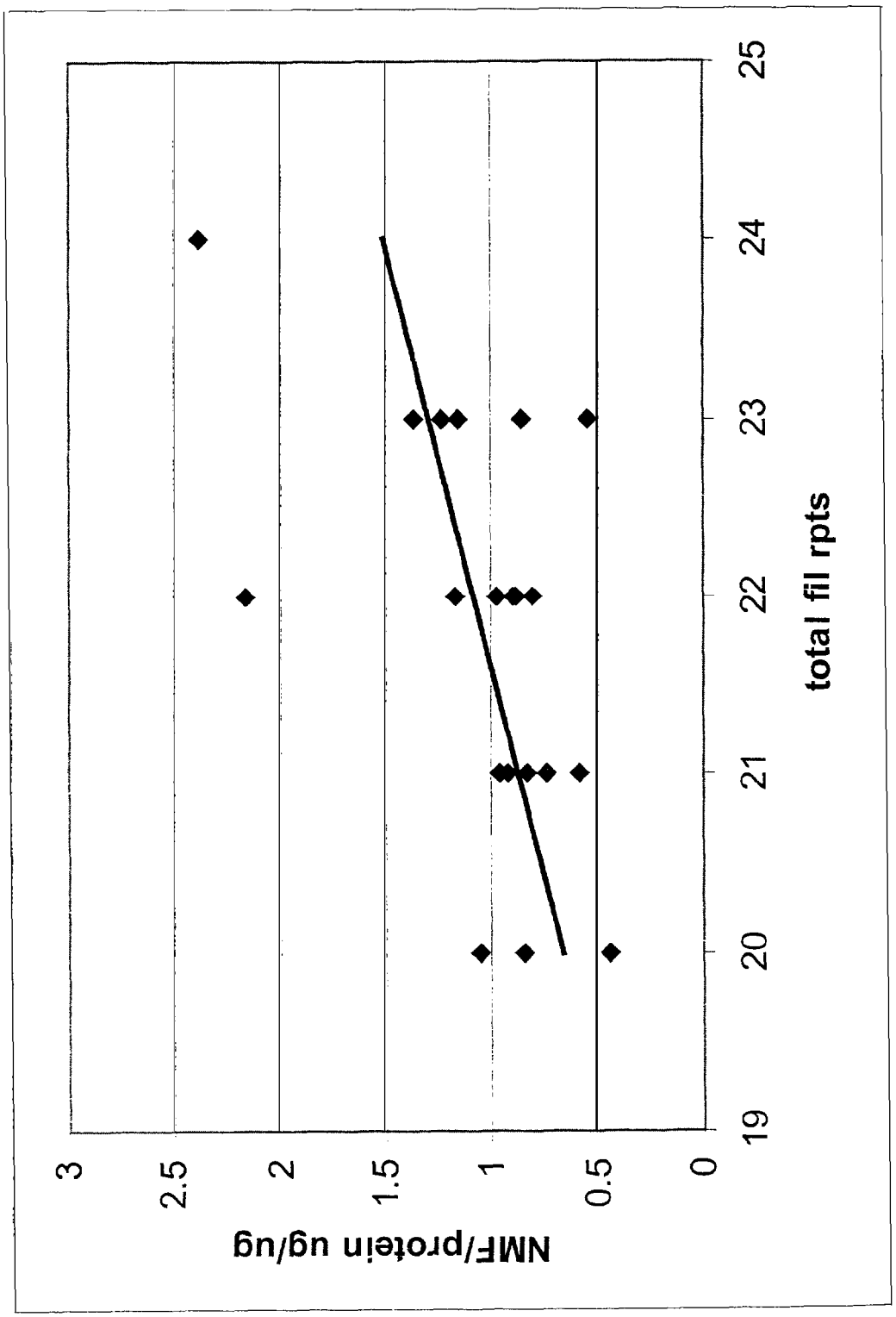
FIG. 2 shows the filaggrin repeat number per chromosome pair versus stratum corneum NMF levels. Spearman correlation: R=0.47; p=0.036; n=20.
Figure 3:
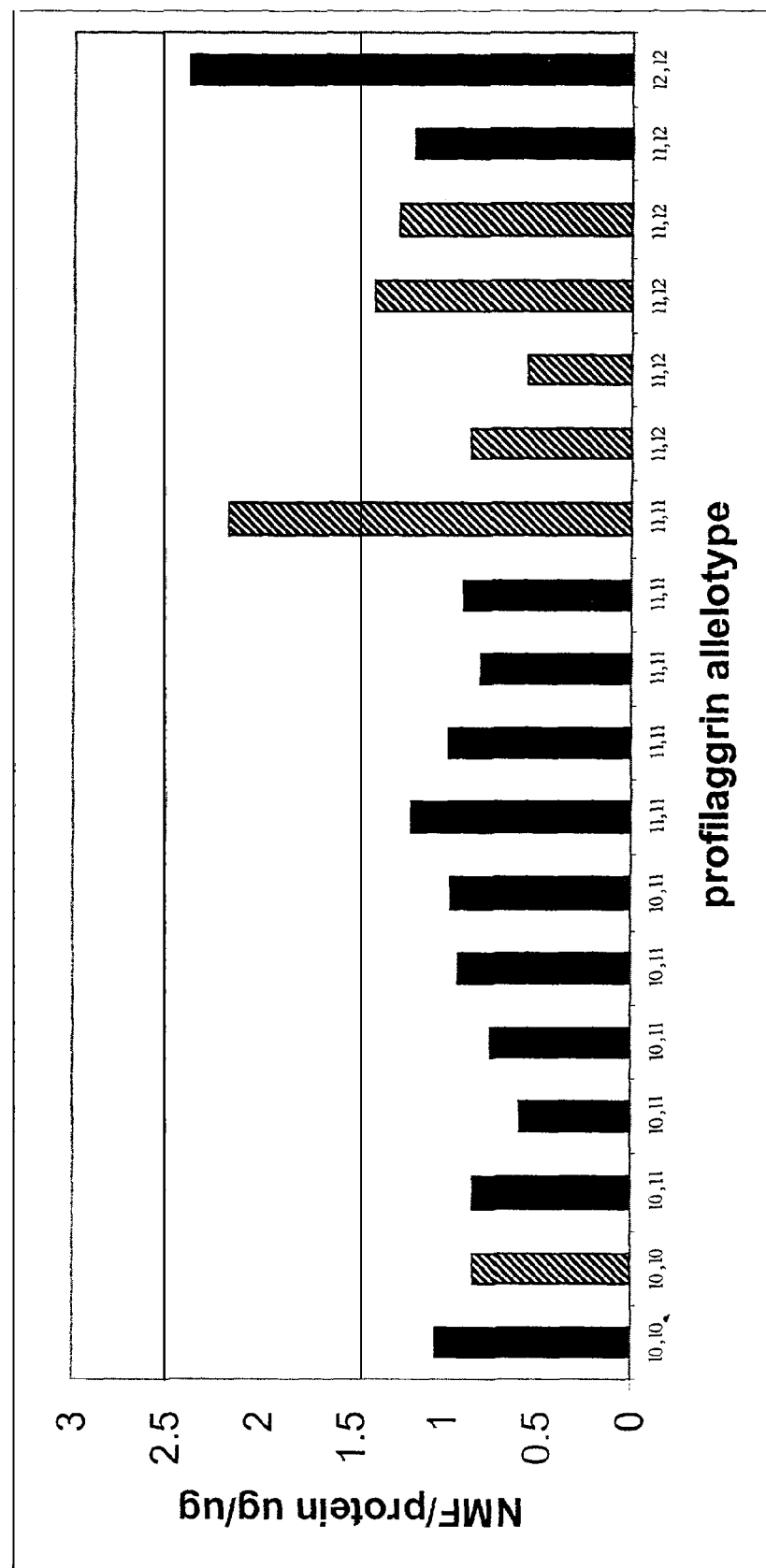
FIG. 3 shows the Filaggrin repeat number per chromosome pair versus stratum corneum NMF levels and including scalp condition history. % dandruff with 1 or more 12 repeat alleles=67%; % dandruff with no 12 repeat alleles=17%

A plot of filaggrin repeat number per chromosome pair versus stratum corneum NMF levels revealed a direct relationship between these two parameters (FIG. 2). Individuals with higher repeat numbers had higher NMF levels. The skin/scalp condition history revealed that individuals who claimed to have suffered from dandruff carried 1 or more copies of the 12 repeat allele (FIG. 3). These results suggest an association between the-presence of the 12 repeat allele in the genome of an individual and susceptibility to dandruff.

A plot of erythemal score after SLS patch (FIG. 4) revealed that individuals carrying 1 or more 12 repeat alleles had lower erythemal scores 48 hours after challenge. These results suggest an association between the presence of the 12 repeat allele and recovery of the skin barrier after detergent challenge.

Example 2

A group of 140 randomly selected panellists provided saliva samples for DNA analysis, and information on skin condition history. On the basis of responses to the questionnaire panellists were assigned self-perceived dry skin frequency—'Frequent' (including always, daily and weekly), and 'Infrequent' (monthly or less often). Visual assessments of the condtion of panellists untreated leg skin were made on 5 consecutive days and panellists grouped as 'No skin dryness' (3 or more assessments with no visual dryness) or 'Skin dryness' (more than 2 assessments with visual dryness). Panellists were subjected to a patch of 1% SLS for 24 hours and the degree of erythema was scored at 4, 24 and 48 hours after the patching. Genomic DNA was extracted from the saliva samples and analysed by PCR to determine the profilaggrin genotype for each individual (FIG. 1).

All three variants were identified with the following frequencies:
10 repeats (24%), 11 repeats (56%), and 12 repeats (20%).

The proportion of panellists of panellists with at least one 12 repeat allele who claimed to suffer from frequent dry skin was only 6% compared with 27% of panellists with no 12 repeat alleles (FIG. 5). This demonstrated that the 12 repeat allele is associated with a reduced tendency to report self-perceived dry skin.

The proportion of panellists with at least one 11 repeat allele who displayed visual leg dryness was 73% compared with only 52% of panellists with no 11 repeat allele (FIG. 6). This demonstrated that the 11 repeat allele is associated with an increased tendency to visual leg dryness.

The proportion of panellists with at least one 12 repeat allele who showed a decrease in erythema between 4 and 48 hours post SLS patch was 66% compared with only 47% of panellists with no 12 repeat alleles (FIG. 7). This again demonstrated that the 12 repeat allele is associated with an increased tendency of the skin to recover after detergent challenge.

The invention claimed is:

1. A method of correlating an individuals levels of profilaggrin alleles present in genome that correspond to different filaggrin repeat lengths with the individuals predisposition for dry skin as measured by either their self-perceived frequency of dry skin, their clinically assessed leg dryness or their recovery to SLS-induced erythema, said method comprising the steps of:
  i) selecting a group of individuals;
  ii) identifying in each individual the proportions of profilaggrin alleles corresponding to 10, 11 or 12 filaggrin repeat units encoded by the genome by analysis of an ex-vivo sample taken from the individual;
  iii) determining for each individual a measure of predisposition for dry skin by correlating the presence of profilaggrin alleles having either the 11 or 12 filaggrin repeat units with susceptibility to dry skin as measured by one or more of the following methods:
     a. recording the individual's self-perceived frequency of dry skin,
     b. clinically assessing the individual's leg dryness, or
     c. determining an individual's rate of recovery following an SLS patch test.

2. The method according to claim 1 wherein the correlations are determined between the proportion of the individuals having profilaggrin alleles having no 11 or 12 filaggrin repeat units and either the number of individuals having frequent self-perceived dry skin, the number of individuals having leg dryness, or the number of individuals exhibiting defined rates of recovery to the SLS patch test.

3. The method according to claim 1 wherein the ex-vivo sample is a sample collected from the oral cavity.

4. The method according to claim 1 wherein the analysis of the ex-vivo sample in step ii) is carried out by:
  (a) providing, as a substrate, DNA from the ex-vivo sample;
  (b) amplifying defined regions of the substrate, which defined regions comprise filaggrin repeat coding sequence; and
  (c) determining the profilaggrin alleles present in the genome of the sample by determining the size or sizes of the thus produced amplification product or products.

5. The method according to claim 4 wherein step (b) is performed by polymerase chain reaction (PCR).

6. The method according to claim 5 comprising providing a pair of oligonucleotides having sequences that can hybridise to the substrate DNA at positions flanking a filaggrin repeat coding sequence.

7. The method according to claim 6 wherein one of the pair of oligonucleotides has the sequence SEQ ID No.1.

8. The method according to claim 6 wherein one of the pair of oligonucleotides has the sequence SEQ ID No.2.

9. The method according to claim 4 wherein amplification is performed using from 0.1 to 30 ng/ml DNA substrate, from 2 μM to 2 mM dNTPs, from 2 μM to 2 mM forward and reverse primers, and from 17 μM to 170 mM $Mg^{2+}$.

* * * * *